United States Patent
Josephy et al.

(10) Patent No.: US 12,280,250 B2
(45) Date of Patent: *Apr. 22, 2025

(54) COOLED MECHANICAL CIRCULATORY SUPPORT SYSTEM AND METHOD OF OPERATION

(71) Applicant: ABIOMED, Inc., Danvers, MA (US)

(72) Inventors: Noam Josephy, Danvers, MA (US); Jerald Curran, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/594,382

(22) Filed: Mar. 4, 2024

(65) Prior Publication Data

US 2024/0316337 A1    Sep. 26, 2024

Related U.S. Application Data

(63) Continuation of application No. 16/852,433, filed on Apr. 18, 2020, now Pat. No. 11,944,803.
(Continued)

(51) Int. Cl.
*A61M 5/00* (2006.01)
*A61F 7/12* (2006.01)
(Continued)

(52) U.S. Cl.
CPC .......... *A61M 60/422* (2021.01); *A61M 60/13* (2021.01); *A61M 60/135* (2021.01);
(Continued)

(58) Field of Classification Search
CPC . A61F 7/12; A61M 1/369; A61M 2205/3368; A61M 2205/3606;
(Continued)

(56) References Cited

U.S. PATENT DOCUMENTS

| 5,749,855 A | 5/1998 | Reitan |
| 6,607,517 B1 | 8/2003 | Dae et al. |

(Continued)

FOREIGN PATENT DOCUMENTS

| CN | 104427948 | 3/2015 |
| CN | 107080870 A | 8/2017 |

(Continued)

OTHER PUBLICATIONS

Office Action from Chinese Patent Application No. 202080039190.1, dated Dec. 6, 2023 (25 pp.).

(Continued)

*Primary Examiner* — Jon Eric C Morales
(74) *Attorney, Agent, or Firm* — Botos Churchill IP Law LLP

(57) ABSTRACT

A mechanical circulatory support system for a heart having a cooling element and a method for using the system to treat the effects of a cardiac episode. The support system has a pump comprising a rotor, the rotor having at least one blade. The system also has a catheter having an inner surface and an outer surface, the catheter extending proximally of relative to the pump housing. The outer surface of the catheter is configured to contact blood when disposed within patient vasculature. The outer surface of the catheter comprises a heat transfer surface configured for cooling blood that comes in contact with the outer surface. The support system is operated to provide a temperature selected to cool the circulating blood in contact with the outer surface of the catheter to a temperature selected to reduce or prevent an effect of a cardiac episode.

18 Claims, 5 Drawing Sheets

Related U.S. Application Data

(60) Provisional application No. 62/836,534, filed on Apr. 19, 2019.

(51) Int. Cl.
    *A61M 60/13* (2021.01)
    *A61M 60/135* (2021.01)
    *A61M 60/148* (2021.01)
    *A61M 60/17* (2021.01)
    *A61M 60/216* (2021.01)
    *A61M 60/36* (2021.01)
    *A61M 60/422* (2021.01)
    *A61M 60/857* (2021.01)
    *A61M 60/865* (2021.01)

(52) U.S. Cl.
CPC .......... *A61M 60/148* (2021.01); *A61M 60/17* (2021.01); *A61M 60/216* (2021.01); *A61M 60/36* (2021.01); *A61M 60/857* (2021.01); *A61M 60/865* (2021.01); *A61M 2205/3368* (2013.01); *A61M 2205/3606* (2013.01); *A61M 2205/366* (2013.01); *A61M 2205/3673* (2013.01)

(58) Field of Classification Search
CPC .... A61M 2205/366; A61M 2205/3673; A61M 60/113; A61M 60/13; A61M 60/135; A61M 60/148; A61M 60/17; A61M 60/216; A61M 60/36; A61M 60/422; A61M 60/857; A61M 60/865
See application file for complete search history.

(56) References Cited

U.S. PATENT DOCUMENTS

| | | |
|---|---|---|
| 7,022,100 B1 | 4/2006 | Aboul-Hosn et al. |
| 7,211,066 B1 | 5/2007 | Merrill |
| 9,180,236 B2 | 11/2015 | Dae et al. |
| 11,944,803 B2 * | 4/2024 | Josephy ............ A61M 60/36 |
| 2001/0044644 A1 | 11/2001 | Keller et al. |
| 2002/0045925 A1 | 4/2002 | Keller et al. |
| 2002/0161351 A1 | 10/2002 | Samson et al. |
| 2003/0060863 A1 | 3/2003 | Dobak |
| 2006/0161095 A1 | 7/2006 | Aboul-Hosn et al. |
| 2011/0152855 A1 | 6/2011 | Mayse et al. |
| 2018/0169312 A1 | 6/2018 | Barry |

FOREIGN PATENT DOCUMENTS

| | | |
|---|---|---|
| EP | 3446729 A1 | 2/2019 |
| JP | H08500512 A | 1/1996 |
| JP | 2001517966 A | 10/2001 |
| JP | 2005507695 A | 3/2005 |
| JP | 2008178690 A | 8/2008 |
| JP | 2010158531 A | 7/2010 |
| JP | 2018536447 A | 12/2018 |
| WO | 9725011 A1 | 7/1997 |
| WO | 0117581 A2 | 3/2001 |
| WO | 0207625 A2 | 1/2002 |
| WO | 03037158 A2 | 5/2003 |
| WO | 2018118756 A1 | 6/2018 |
| WO | 2018139508 A1 | 8/2018 |

OTHER PUBLICATIONS

Office Action from Japanese Patent Application No. 2021-561897, dated Dec. 26, 2023 (10 pp.).
Office Action from Chinese Patent Application No. 20208003919091 dated Jun. 20, 2024 (11 pp.).
Office Action from Israeli Patent Application No. 287284 dated Jun. 9, 2024 (3 pp).
International Search Report and Written Opinion for Application No. PCT/US2020/028876 dated Jul. 20, 2020.
Office Action issued in Indian Patent Application No. 202117050328 dated Nov. 28, 2023 (6 pp.).
Office Action from corresponding Australian Patent Application No. 2020257276 dated Nov. 16, 2024 (4 pp.).
Office Action from Korean Patent Application No. 10-2021-7037402 dated Jan. 9, 2025 (23 pp.).

* cited by examiner

402
Introducing a Mechanical Circulatory Support Device into a Vasculature of a Patient, the Support Device Comprising a Cooling Element within a Catheter;

404
Positioning the Catheter within the Vasculature so that an Outer Surface of the Catheter Contacts Blood Flowing within the Vasculature;

406
Actuating the Mechanical Circulatory Support Device to Circulate Blood within the Patient;

408
While Actuating the Mechanical Circulatory Support Device, Activating the Cooling Element to Cool the Outer Surface of the Catheter for a Period of Time to a Temperature Selected to Cool the Circulating Blood in Contact with the Outer Surface of the Catheter to the Systemic Temperature.

FIG. 4

502 — Introducing a Mechanical Circulatory Support System into the Vasculature of a Patient, the Mechanical Circulatory Support System Comprising a Cooling Element within a Catheter, wherein the Cooling Element is a Fluid-bearing Lumen Configured to Receive a Chilled Solution;

504 — Positioning the Catheter within the Vasculature so that an Outer Surface of the Catheter Contacts Blood Flowing within the Vasculature, 506 — Actuating the Mechanical Circulatory Support System;

508 — While Actuating the Support System, Injecting the Chilled Solution into the Fluid-bearing Lumen to Cool the Outer Surface of the Catheter for a Period of Time to a Temperature Selected to Cool the Circulating Blood in Contact with the Outer Surface of the Catheter to the Systemic Temperature.

FIG. 5

602 — Introducing a Mechanical Circulatory Support System into the Vasculature of a Patient, the Mechanical Circulatory Support System Comprising a Cooling Element within a Catheter, wherein the Cooling Element is a Conductor Affixed to a Current-bearing Wire Configured to Receive an Electric Current;

604 — Positioning the Catheter within the Vasculature so that an Outer Surface of the Catheter Contacts Blood Flowing within the Vasculature,

606 — Actuating the Mechanical Circulatory Support System;

608 — While Actuating the Mechanical Circulatory Support System, Running an Electric Current Through the Current-bearing Wire to a Junction of Two Dissimilar Conductors to Reduce or Prevent an Effect of a Cardiac Episode.

FIG. 6

COOLED MECHANICAL CIRCULATORY SUPPORT SYSTEM AND METHOD OF OPERATION

CROSS-REFERENCE TO RELATED APPLICATIONS

This application is a continuation of U.S. application Ser. No. 16/852,433, filed Apr. 18, 2020, now U.S. Pat. No. 11,944,803, which application claims the benefit of U.S. Provisional Patent Application No. 62/836,534, filed Apr. 19, 2019, entitled "Cooled Impella," the disclosures of all of which are hereby incorporated by reference in their entirety.

BACKGROUND OF THE INVENTION

Mechanical circulatory support systems, such as intracardiac or intravascular blood pumps may be introduced in the heart to deliver blood from the heart into an artery. Such mechanical circulatory support devices are often introduced to support the function of the heart after a patient suffers a cardiac episode. One such class of devices is the set of devices known as the "Impella" heart pump. Some blood pump assemblies may be introduced percutaneously through the vascular system during a cardiac procedure. Specifically, blood pump assemblies can be inserted via a catheterization procedure through the femoral artery or the axillary/subclavian artery, into the ascending aorta, across the aortic valve, and into the left ventricle. The inserted blood pump assembly may be configured to pull blood from the left ventricle of the heart through a cannula and to then expel the blood into the aorta. A blood pump assembly may also be configured to pull blood from the inferior vena cava and to then expel blood into the pulmonary artery. Some mechanical circulatory support devices are powered by an on-board motor, while others are powered by an external motor and a drive cable. Still other blood pumps use an external pump, positioned outside the patient, and a long catheter that extends through the vasculature and into the heart or other desired location. Some blood pump systems are implanted surgically, rather than by catheter.

The cardiac episodes that necessitate the use of a blood pump may typically cause a multitude of detrimental effects to the patient. Such cardiac episodes include myocardial infarction, cardiac arrest, high-risk percutaneous coronary interventions, cardiogenic shock, and left—and right-ventricular failure. In particular, a patient experiencing myocardial infarction, more commonly referred to as a heart attack, can be left with extensive scarring on their heart tissue. Such scarring alters the normal conduction pathways of the heart, and weakens the affected muscles. Depending on the size and location of the scarring, a patient may be at an increased risk for arrhythmias, heart block, ventricular aneurysms, heart wall inflammation, and rupture of the heart wall, all of which can be fatal. Reducing or preventing such myocardial scarring is therefore highly desirable.

SUMMARY OF THE INVENTION

One known method of treating myocardial infarction scarring is induced systemic hypothermia, in which the blood flowing through the heart of a patient is rapidly cooled to a desired systemic temperature. For example, a desired systemic temperature may be lower than (e.g., 5 degrees Celsius below) a patient's normal body temperature. A sufficient temperature decrease in the blood to the desired systemic temperature via systemic hypothermia cools the heart and thereby slows a number of physiological processes within the heart, such as metabolic reactions, tissue death, and myocardial scarring. However, the current use of induced systemic hypothermia is known to cause arrhythmia in patients, which is particularly problematic in patients suffering from myocardial scarring, whose hearts are already increasingly weakened. Thus, to minimize the undesirable effects of myocardial scarring, as well as to minimize undesirable effects of induced hypothermia, it is desirable to have a system that is capable of simultaneously systemically cooling blood flow in order to prevent or reduce myocardial scarring while also preventing arrhythmias.

The systems, methods, and devices described herein provide mechanical circulatory support systems, e.g. blood pump systems, configured to simultaneously unload the heart while systemically cooling the blood of the patient. The blood contacting surface of the blood pump or other circulatory support system can be configured as a heat transfer surface to perform the systemic cooling. When a heat transfer surface of a catheter of the pump system is brought into contact with the blood circulating through the vasculature of a patient, the blood can be rapidly cooled, and the cooling may remove sufficient heat from the blood to induce a systemic hypothermic effect in the patient. The induced hypothermic effect slows down the biological processes that cause or exacerbate undesirable effects of cardiac episodes. However, as inducing systemic hypothermia may cause arrhythmias, the hypothermia therapy is induced concurrently with the standard operation of a blood pump or other circulatory support system. In this manner, the induced systemic hypothermia may reduce (or reverse) the undesirable effects of cardiac episodes while the blood pump or other circulatory support system circulates blood within the vasculature, thereby increasing the nourishment of the heart (and other vasculature) to prevent or avoid the undesirable effects of induced systemic hypothermia. The systems, methods, and devices described herein can be used to treat various vascular pathologies, including, but not limited to, myocardial infarction, cardiac arrest, high-risk percutaneous coronary interventions, cardiogenic shock, and left—and right-ventricular failure. In many adaptations, the systems described herein are blood pump systems for simultaneously cooling and providing mechanical circulatory support to the heart (e.g., by unloading the heart). In general, a blood pump system has a pump with a rotor having at least one blade that turns within a pump housing that surrounds the blade(s). In general, the pump is driven by a motor. Some pumps are powered by an on-board motor, while others are powered by an external motor and a drive cable. Other pump systems have an external pump, positioned external to the patient, and a long catheter (or cannula) that extends intravascularly to the heart (or other position in the vasculature). Adaptations of the presently disclosed systems may further include a catheter extending from a proximal end of the pump. Other adaptations may include surgically installed pump systems. In some implementations, a flexible, atraumatic projection extends from the distal end of the pump. For example, the flexible, atraumatic projection may be a pigtail.

According to some aspects, the systems described herein include an intravascular cooling surface that induces hypothermia. The cooling surface is configured to extend along a length of the catheter or other intravascular surface of the system and be positioned within the vasculature to contact blood while it is circulating within a patient. In some implementations, the cooling element may be formed as a heat exchanger for the blood and may function by cooling an outer surface of the catheter, which then cools the blood circulating through the vasculature of the patient as the blood contacts the outer surface of the catheter. A similar cooling system may be applied to other portions of the blood-contacting surface of the support system (e.g., the pump housing), either in lieu of the catheter or to augment the heat transfer effects of the catheter. In some adaptations, the heat transfer element is applied directly to the outer surface of the catheter (or other system component), so that the outer surface of the catheter (the blood contacting surface) is cooled directly; in such implementations, blood may directly contact the heat transfer element. In other adaptations, the heat transfer occurs indirectly by positioning the heat transfer element within the thickness of the catheter wall, or along the inner surface of the catheter, so it first cools the inner or thickness of the wall of the catheter, and that thickness or inner surface cools the outer surface of the catheter by conduction through the catheter wall thickness.

At least one advantage of the incorporation of a cooling element into the pump system is the ability to adjust blood (and systemic vascular) temperature to prevent undesirable effects of a cardiac episode while simultaneously preventing the undesirable effects of the adjusted temperature (e.g., induced systemic hypothermia).

According to a first embodiment of the disclosure, a blood pump system for a heart includes a pump. The pump has a motor and a rotor, and a heat transfer surface that is configured to be inserted within the patient and thermally adjusted, for example by a cooling element. The pump has a distal end and a proximal end. In general, the rotor has at least one blade for conveying blood through the pump. In some implementations, the cooling element may be configured as a lumen to provide thermofluidic cooling, with the lumen being configured to deliver a chilled solution along a length of the catheter. In other implementations, the cooling element may be configured as a Peltier device to provide thermoelectric cooling, with the Peltier device configured to deliver a current flow along a length of the catheter. The Peltier device may include wires that are configured to deliver current to a junction of two semiconductor materials. The junction of the semiconductors may be disposed at any suitable point along the length of the catheter. Similarly, the semiconductors may be oriented in any suitable configuration so as to induce the desired heat flow along the length of the catheter. In some implementations, the power supply that delivers the current to the Peltier device is the same as a power supply that powers the pump. In other implementations, the power supply that delivers the current to the Peltier device is an external power supply that is different from the power supply that powers the pump.

The system further includes a pump housing, the pump housing surrounding the at least one blade of the rotor. In intravascular applications, a catheter extends from the proximal end of the pump housing. The catheter has an inner surface and an outer surface, as well as a proximal end and a distal end. Blood flows over the outer surface of the catheter when the catheter is disposed within the vasculature of the patient. The pump system may alternatively be installed surgically, without a catheter, and the pump (or its cannula) may have the Peltier or other cooling element configuration.

In the catheter applications, the cooling element extends along a length of the catheter, and the cooling element may be arranged in a variety of configurations. The cooling element may have a circular, elliptical, rhomboidal, rectangular, linear, or other shape cross-section. The geometry of the cross-section can be adjusted in order to adjust the percentage of the inner surface of the catheter that is in contact with the cooling element. For example, in implementations having circular cross-sections, if the area of the cross-section is increased, a greater portion of the inner surface of the catheter is in contact with the cooling element and the rate of heat transfer as well as a total amount of heat transferred can be increased.

According to some aspects, a cooling element may be in contact with a catheter or other blood-contacting system component to provide thermal control of the component, and thus provide a desired thermal control and/or adjustment (e.g., cooling) of the blood. The cooling element may also be configured to increase in temperature, for example, to increase the temperature of the blood, if desired. To cool the vasculature, the cooling element cools the blood contacting surface of the catheter (or other system component) to a temperature that is less than the systemic temperature of the blood. For example, in many applications the temperature to which the blood contacting surface of the catheter is cooled may be about 32 degrees Celsius). In some embodiments the cooling element is in contact with the outer surface of the catheter or other system component. In other embodiments the cooling element is in contact with a portion of the inner surface of the catheter (either via a side-lumen or embedded within the walls of the catheter or other system component), and in those embodiments the cooling element cools the inner surface of the catheter to the lower temperature which then cools the outer surface of the catheter by conduction. In some implementations, the cooling element can extend along a length of the catheter, and may then further extend into another system component. For example, another system component into which the cooling element can extend is the pump housing. The outer surface of the catheter may thus be indirectly cooled to a desired temperature (e.g., less than the systemic blood temperature), and the outer surface can then cool the blood in contact with the outer surface of the catheter or other system component. The blood in the heart is cooled until a desired systemic temperature is reached. The cooling may be done rapidly. For example, the blood may be systemically cooled for a time period of between about 5 minutes and about 20 minutes. In other implementations, the time period is between about 7.5 minutes and about 17.5 minutes. In further implementations, the time period is between about 10 and about 15 minutes. In some implementations, the time period is about 12.5 minutes. In certain implementations, the blood is cooled in less than 5 minutes. In other implementations, the blood is cooled in less than 3 minutes.

In certain implementations, the systemic temperature to which the blood is cooled, is less than 37 degrees Celsius. In some implementations, the systemic temperature to which the blood is cooled is between about 30 degrees and about 35 degrees Celsius. In other implementations, the systemic temperature to which the blood is cooled ranges between about 31 degrees and about 34 degrees Celsius. In further implementations, the systemic temperature to which the blood is cooled is between about 32 degrees and about 33 degrees Celsius. The cooling of the blood circulating within a patient provides a hypothermic effect which slows down the biological processes responsible for causing or exacerbating negative effects of cardiac episodes. Specifically, the cooling of the blood can slow the processes responsible for causing myocardial scarring to the heart of a patient after the patient suffers from myocardial infarction, while the simultaneous pumping of the heart prevents the negative effects that are known to be induced by induced systemic hypothermia therapies.

In some implementations, the cooling element may be configured as aa lumen, and the lumen may be configured to deliver a chilled solution along a length of the catheter. Injection of the chilled solution into the lumen may induce a hypothermic effect in a patient. To deliver this hypothermic effect, at least a portion of the lumen may be a side lumen in contact with a portion of the inner surface of the catheter. Alternatively, at least a portion of the lumen may be embedded within a wall of the catheter. The specific portion of the lumen that is selected to be in contact with the inner surface of the catheter or that is selected to be embedded in the wall of the catheter can be selected in order to implement a desired rate of heat transfer along a portion of the catheter. Specific heat transfer rates at different areas along the length of the catheter may be beneficial for the treatment of the negative effects of certain cardiac episodes. For example, in some implementations, half of the lumen may be in contact with a portion of the inner surface of the catheter. In other implementations, three quarters of the lumen may be in contact with a portion of the inner surface of the catheter. Similarly, half of the lumen may be embedded within the wall of the catheter. In other implementations, three quarts of the lumen may be embedded within the wall of the catheter. A heat transfer surface of the catheter is cooled when the flow of the chilled solution cools the inner surface of the catheter. The heat transfer surface of the catheter subsequently cools the blood, inducing a hypothermic effect in the patient. The lumen has a first proximal opening and a second proximal opening. The first proximal opening may be configured as an inlet for a chilled solution, and the second proximal opening may be configured as an outlet for the chilled solution. The lumen may be configured to include two portions—a first flow portion and a second flow portion, both portions extending along a length of the catheter. The first flow portion extends from the first proximal opening to the distal end of the catheter, and accommodates flow of the chilled solution in the distal direction, from the proximal end of the catheter to the distal end of the catheter. The second flow portion extends from the distal end of the catheter to the second proximal opening, and accommodates flow of the chilled solution in the proximal direction, from the distal end of the catheter to the proximal end of the catheter. The first and second flow portions may extend along equal lengths of the catheter. The first flow portion may be from the first proximal opening at the proximal end of the catheter to the distal end of the catheter, and defines a first lumen path length along which the lumen extends.

The first lumen path length may be equal to the length of the catheter along which the lumen extends. The second flow portion may be from the distal end of the catheter to the second proximal opening at the proximal end of the catheter, and defines a second lumen path length along which the lumen extends. The second lumen path length may be equal to the length of the catheter along which the lumen extends. In some implementations, the first lumen path length may be greater than the second lumen path length. In other implementations, the first lumen path length may be equal to the second lumen path. The length of the catheter along which the lumen extends may be three quarters of the length of the catheter. In other implementations, the length of the catheter along which the lumen extends may be one half the length of the catheter. In certain implementations, the lumen extends along the entire length of the catheter. The length of the catheter along which the lumen extends allows chilled solution to be delivered along the same length of the catheter. In such implementations, after the chilled solution is injected into the first proximal opening, and after the fluid has extended along first flow portion, it extends along the second flow portion, and exits the system from the second proximal opening. At least one advantage of a blood pump configured with a lumen to receive a chilled solution is that the pump may simultaneously induce systemic hypothermia to treat the undesirable effects of a cardiac episode while also unloading the heart in order to treat the undesirable effects of systemic hypothermia, including arrhythmias.

The lumen may be configured within the catheter in a variety of different ways. In certain implementations, the lumen may be configured to be in contact with an inner surface of the catheter. For example, the lumen may be configured to contact an inner surface of the catheter as it extends along the first flow portion, the first flow portion defining the first lumen path length. The first flow portion can extend along any suitable path, including, but not limited to, a straight line or a helix. The lumen may then be configured to extend along the second flow portion through the center of the catheter, the second flow portion defining the second lumen path length. In other implementations, a portion of the lumen may be embedded within the wall of the catheter. For example, the first flow portion of the lumen may be embedded in the wall of the catheter while the second flow portion extends through the center of the catheter. In other implementations, the first flow portion of the lumen may extend through the center of the catheter while the second flow portion is embedded in the wall of the catheter. In certain implementations, both the first flow portion and the second flow portion are embedded in the wall of the catheter. The second flow portion may also be configured in a variety of geometries, also including, but not limited to, a straight line or a helix. Keeping the second flow portion out of contact with the inner surface of the catheter keeps the solution that has already absorbed heat from the blood away from the inner surface of the catheter allows for a more rapid temperature decrease in the blood. The specific orientation of the lumen within the catheter may be adjusted in order to direct heat both to and from different areas along the length of the catheter.

Additionally, the flow of the chilled solution may be reversibly configured within the lumen. As discussed above, the lumen may be configured to extend along a length of the catheter from the first proximal opening at the proximal end of the catheter to the distal end of the catheter. The lumen may extend along the length of the catheter in various ways. In some implementations, a portion of the lumen may be in contact with the inner surface of the catheter. In other implementations, a portion of the lumen may be embedded within a wall of the catheter. Generally, the lumen is configured to receive a chilled fluid. The chilled fluid cools a surface of the catheter, which, by the conduction of heat, cools a heat transfer surface of the catheter. This heat transfer surface induces a systemic effect in the blood of a patient. In such implementations, chilled solution may be injected into the first proximal opening, allowing the first proximal opening to function as an inlet for the chilled solution, and allowing the chilled solution to flow along the first flow portion from the proximal end of the catheter to the distal end of the catheter. In such implementations, the fluid travels to the second proximal opening along the second length of the catheter, from the distal end of the catheter to the proximal end of the catheter, allowing the second proximal opening to function as an outlet for the chilled solution. As the flow of the chilled solution may be reversibly configured within the lumen, in other implementations, the chilled solution is first injected into the second proximal opening, allowing the second proximal opening to function as an inlet for the chilled solution, and allowing the chilled solution to flow along the second flow portion from the proximal end of the catheter to the distal end of the catheter. In such implementations, the fluid returns to the first proximal opening along the first flow portion, from the distal end of the catheter to the proximal end of the catheter, allowing the first proximal opening to function as an outlet for the chilled solution. This reversibility of the flow of the chilled solution applies to all embodiments containing a lumen.

In some implementations, the path formed by the lumen as it extends from one end of the catheter to the other end is a helix. For example, the lumen may form a single helix as it extends along the first flow portion. A single helix is herein defined as a single strand (e.g. a single lumen, wire, or semiconductor) that is shaped as a helix. The lumen may then be configured to return along the second flow portion through the center of the catheter. In other implementations, this situation may be reversed. Specifically, the lumen may extend along the first flow portion through the center of the catheter. The lumen may then be configured to return along the second flow portion in a helix. As previously discussed, the specific geometry of the lumen within the catheter can serve to direct heat to and from specific areas of the catheter. The direction of heat can therefore be controlled in order to create a particular heat distribution along the catheter. For example, certain patient pathologies or anatomies may benefit from a particular heat distribution. In configurations wherein a single helix is in contact with the inner surface of the catheter, one advantage is that the blood can be cooled rapidly, as the flow direction of the chilled solution through the lumen may be selected such that no fluid that has absorbed heat from the blood is in contact with the inner surface of the catheter. At least one advantage of mechanical circulatory support devices (e.g., blood pumps) having a lumen extending along a helix along the length of the catheter is that such pumps can efficiently cool the blood to induce systemic hypothermia to treat negative effects of cardiac episodes while also supporting the heart to counteract the negative effects of induced systemic hypothermia.

In other implementations, the lumen extends along a helix in both directions. The lumen extends along the first flow portion along a first helix, and the lumen extends along the second flow portion along a second helix. The first helix and the second helix of the lumen are in fluid communication at the distal end of the catheter. In such implementations, the first helix and the second helix may be offset by an angle along the circumference of the catheter so as to form a double helix. A double helix as defined herein comprises two helices of the same pitch and radius that are oriented 180 degrees from each other along the circumference of the catheter. In implementations in which the first helix and the second helix are not offset by an angle along the circumference of the catheter, the first helix and the second helix form a double-wide single helix. A double-wide single helix as defined herein as comprises two single helices of the same pitch and of the same radius that are in contact at every point along their lengths. In other implementations, the first helix and the second helix may be offset by an intermediate angle along the circumference of the catheter. This intermediate angle may be between 0 degrees and 180 degrees. For example, the first helix and the second helix may be offset by about 45 degrees along the circumference of the catheter. In other implementations, the first helix and the second helix may be offset by about 90 degrees along the circumference of the catheter. In certain implementations, the first helix and the second helix may be offset by about 135 degrees along the circumference of the catheter. At least a portion of the helical element, whether forming a double helix, a double-wide single helix, or any other configuration, is in contact with the inner surface of the catheter.

In some implementations, a pitch of the double helix formed by the cooling element is between about 1 millimeter and about 10 millimeters. In further implementations, the pitch of the double helix formed by the cooling element is between about 3 millimeters and about 8 millimeters. In other implementations, the pitch of the double helix formed by the cooling element is between about 5 millimeters and about 6 millimeters. In certain implementations, the pitch of the double helix formed by the cooling element is about 5.5 millimeters. The variability of the pitch of the helix formed by the cooling element for a specific heat profile and heat transfer profile to be established along the catheter.

In some implementations, the double helix formed by the cooling element covers between about 30 percent and about 90 percent of the inner surface of the catheter. In other implementations, the double helix formed by the cooling element covers between about 40 percent and about 80 percent of the inner surface of the catheter. In certain implementations, the double helix formed by the cooling element covers between about 50 percent and about 70 percent of the inner surface of the catheter. In some implementations, the double helix formed by the cooling element covers about 60 percent of the inner surface of the catheter. Implementations of blood pumps having larger interior surface areas covered by the cooling element allow for the blood to be more rapidly cooled while still providing support to the heart in order to combat the negative effects of induced systemic hypothermia.

In implementations having a lumen configured in a double-helix, the first single helix that extends along the first flow portion and the second single helix that extends along the second flow portion are in fluid communication at the distal end of the catheter. Specifically, the lumen first extends along the first flow portion while extending along a first helix. The lumen may then extend along the second flow portion while extending along a second helix. After the lumen extends along the first flow portion, the lumen extends along a length of the circumference of the catheter at a fixed longitudinal point. The lumen may be in contact with the inner surface of the catheter as it extends along the length of the circumference of the catheter. In double helix configurations, the lumen extends along one half of the circumference of the catheter at a fixed longitudinal point, such that the first and second helices are offset by an angle of 180 degrees along the circumference of the catheter. At least one advantage of implementations having a lumen configured in the shape of a double-helix is that the by varying the pitch of the double helix, different rates of cooling and different heat profiles along the length of the catheter can be implemented.

In other implementations, the lumen forms a double-wide single helix, which, as defined above, comprises two single helices of the same pitch and of the same radius that are in contact at every point along their lengths. In such implementations, the first single helix and the second single helix are in fluid communication. Together, the first single helix along which the lumen extends along the first flow portion and the second single helix along which the lumen extends along the second flow portion create a double-wide single helix. Specifically, the lumen extends along the first flow portion while extending along a first helix. The lumen may then extend along the second flow portion while extending along a second helix. After the lumen extends along the first flow portion, the lumen extends along a length of the circumference of the catheter at a fixed longitudinal point. In double-wide single helix configurations, the lumen extends along an entire circumference of the catheter at a fixed longitudinal point, such that the first and second helices are offset by an angle of 0 degrees along the circumference of the catheter. The pitch of the double-wide single helix may be adjusted to yield a certain heat profile along the catheter.

In some implementations, a chilled solution is injected into the lumen to cool the blood. The chilled solution may comprise a crystalloid fluid. The crystalloid fluid may be Normal saline (a solution comprising 9 grams of sodium chloride per liter of solution), Lactated Ringer's solution, ⅓ NS ⅔D5, or glucose. Generally, the solution with the highest heat capacity is selected, as such a solution will be able to cool the blood most rapidly without experiencing an increase in temperature, allowing the solution to remain in contact with the inner surface of catheter along both lengths of the catheter. Blood pumps having lumens configured to receive a chilled solution can therefore rapidly cool the blood in order to treat the negative effects of cardiac episodes while also unloading the heart to offer support from the negative effects of induced systemic hypothermia.

As an alternative to a cooling element configured as a lumen that delivers chilled solution along a length of the catheter, in some implementations, the cooling element is a Peltier device. The Peltier device may be embedded within the wall of the catheter, or affixed along the outer or inner surface of the catheter. In other implementations, the Peltier device is embedded within the pump housing or other blood-contacting components of the blood pump system. The Peltier device can be fused to the catheter, the pump housing, or another blood-contacting component of the blood pump system. In other implementations, the Peltier device can be attached to the catheter, the pump housing, or another blood-contacting component of the blood pump system with an adhesive. In general, the Peltier device may be configured to direct heat from any combination of the catheter, pump housing, or another component of the blood pump system. The Peltier device drives the transfer of heat between two semiconductor materials having different properties. For example, the electron densities of the two semiconductor materials may be different (e.g., one material may be an n-type semiconductor and the other material may be a p-type semiconductor). The Peltier device can be configured in a variety of geometries. Particularly, the Peltier device comprises two semiconductor materials forming a junction which may be arranged in a variety of different configurations in order to direct heat flow in the desired direction. Generally, the junction may be placed at any suitable point along the length of the catheter in order to implement a desired heat distribution and rate of heat exchange along the length of the catheter. For example, the semiconductor materials may be oriented such that heat flow is directed in a radial direction, or the semiconductor materials may be oriented such that heat flow is directed longitudinally along the length of the catheter. The semiconductor materials may further be arranged in any configuration that allows for a current to be delivered to a junction formed by the semiconductor materials. In some implementations, a power supply that delivers the current to the Peltier device is the same as a power supply that powers the pump. In other implementations, the power supply that delivers the current to the Peltier device is different from the power supply that powers the pump. The delivery of the current to the junction of the semiconductor materials causes cooling by the Peltier effect, in which cooling occurs when a voltage is established at a junction of two semiconductor materials having different electron densities (e.g., an n-type semiconductor and a p-type semiconductor), the junction comprising a first semiconductor material and a second semiconductor material. The application of the Peltier effect causes the semiconductor material that is in contact with an inner surface of the catheter to drop in temperature and act as a heat sink to cool blood that is in contact with an outer surface of the catheter to a systemic temperature. In some implementations, the junction is disposed within the surface of the catheter toward the distal end of the catheter. In other implementations, the junction may be configured within the wall of the catheter towards the proximal end of the conductor.

The first semiconductor material may be configured to twice extend along a length of the catheter. The first length of the catheter along which the semiconductor conductor material extends is generally equal to the second length of the catheter along which the semiconductor material extends. The first length of the catheter along which the semiconductor material extends may be from the proximal end of the catheter to the distal end of the catheter. The second length of the catheter along which the semiconductor material extends may be from the distal end of the catheter to the proximal end of the catheter. The first length of the catheter along which the semiconductor material extends may be three quarters of the length of the catheter from the proximal end of the catheter to the distal end of the catheter, and the second length of the catheter along which the semiconductor material extends may be three quarters of the length of the catheter from the distal end of the catheter to the proximal end of the catheter. At least one advantage of implementations using a Peltier device is the ability to select and incorporate various semiconductor materials, in order to create a specific rate of heat exchange as well as a specific heat distribution along the catheter. The incorporation of a Peltier device to a blood pump therefore offers heart support to overcome the negative effects of induced systemic hypothermia while also allowing systemic hypothermia to be induced in order to treat the negative effects of cardiac episodes.

In implementations having a Peltier device as the cooling element, the current delivered to the junction of the semiconductor materials of the Peltier device may range from between about 0.01 Amperes and about 3 Amperes. In some implementations, a current between about 0.1 Amperes and about 2 Amperes is delivered to the junction of the semiconductor materials of the Peltier device. In further implementations, a current between about 0.5 Amperes and 1.5 Amperes is delivered to the junction of the semiconductor materials of the Peltier device. In certain implementations, a current of about 1 Ampere is delivered to the junction of the semiconductor materials of the Peltier device. The particular current run through the wire of the Peltier device can be adjusted to create a certain potential difference at the junction of the semiconductor materials, allowing for a certain heat distribution and rate of cooling of the blood to be implemented along the catheter.

According to some aspects of the disclosure, a method for treating an effect of a cardiac episode in a patient comprises first introducing into the vasculature of the patient a mechanical circulatory support device. The mechanical circulatory support system may be a blood pump. The blood pump comprises a cooling element, such as a fluid lumen or Peltier device, disposed within a catheter. After introducing the blood pump into the vasculature of the patient, a practitioner executing the method positions the catheter within the vasculature such that an outer surface of the catheter contacts the blood flowing through the vasculature. The practitioner then actuates the blood pump to circulate blood within the patient. While actuating the blood pump, the practitioner activates the cooling element. As previously discussed, the cooling element functions as a heat exchanger by cooling the inner surface of the catheter. The inner surface of the catheter then cools the outer surface of the catheter, which then cools the blood of the patient. This cooling is performed over a period of time selected to ensure that the outer surface of the catheter reaches a selected temperature. The temperature of the outer surface of the catheter is selected such that the blood that is in contact with the outer surface of the catheter is cooled to a systemic temperature. The temperature to which the outer surface is cooled may be less than or equal to the systemic temperature. Specifically, the blood is cooled to a selected systemic temperature in order to treat an effect of a cardiac episode. In some implementations, the cardiac episode may be myocardial infarction, and in some implementations, the effect of the myocardial infarction is myocardial scarring.

In some implementations, a blood pump is inserted into the left side of the heart of the patient such that the system helps to unload the left ventricle of the patient. In other implementations of the method, the blood pump is inserted into the right side of the heart of the patient such that the system helps to unload the right ventricle of the patient.

In certain implementations, a first blood pump is introduced to one side of the heart of the patient and a second blood pump is introduced to the other side of the heart of the patient. In some implementations, the first blood pump is introduced into the right side of the heart of the patient, and the second blood pump is introduced into the left side of the heart of the patient. In other implementations, the first blood pump is introduced into the left side of the heart of the patient, and the second blood pump is introduced into the right side of the heart of the patient. Such implementations comprise simultaneously cooling the blood and unloading both sides of the heart of the patient. Simultaneously cooling the blood and unloading both sides of the heart may allow the practitioner to cool the heart even more rapidly than by cooling on one side while concurrently supporting the heart to prevent undesirable effects of induced systemic hypothermia.

In another embodiment, a method for treating an effect of a cardiac episode in a patient comprises first introducing into the vasculature of the patient a mechanical circulatory support device, the mechanical circulatory support device comprising a lumen configured within a catheter. The mechanical circulatory support device of the method may be a blood pump. After introducing the blood pump into the vasculature, a practitioner executing the method of the embodiment positions the catheter within the vasculature of the patient such that an outer surface of the catheter contacts blood flowing within the vasculature. Once the blood pump is properly positioned, the practitioner actuates the blood pump, and while the system is actuated, the practitioner injects into the lumen a chilled solution. The injection of the chilled solution into the lumen cools the outer surface of the catheter for a period of time to a temperature, the temperature of the outer surface of the catheter being selected such that the circulating blood in contact with the outer surface of the catheter cools to a systemic temperature. The temperature to which the outer surface of the catheter is cooled may be less than or equal to the systemic temperature. The systemic temperature is selected to reduce or prevent an effect of a cardiac episode. In some implementations, the cardiac episode is myocardial infarction, and the effect of the myocardial infarction is myocardial scarring. Such implementations provide an advantage that the chilled solution inserted into the lumen can induce systemic hypothermia in the blood of a patient in order to treat or prevent a negative effect of a cardiac episode while the pump circulates blood within the patient (e.g., by unloading the heart) in order to prevent the negative side effects that can be caused by induced systemic hypothermia therapies.

In another embodiment, a method for treating an effect of a cardiac episode in a patient comprises first introducing in the vasculature of the patient a mechanical circulatory support device. The mechanical circulatory support device may be a blood pump. The blood pump of the embodiment comprises a Peltier device configured within a catheter, the Peltier device comprising a junction of two semiconductor materials having different electron densities. After introducing the blood pump into the vasculature, a practitioner executing the method of the embodiment positions the catheter within the vasculature of the patient such that an outer surface of the catheter contacts blood flowing within the vasculature. Once the blood pump is properly positioned, the practitioner actuates the blood pump, and while the blood pump is actuated, the practitioner runs a current through the first wire. By the Peltier effect, in which current flowing between a junction of two semiconductor materials allows for the removal of heat from one of the semiconductor materials, the cooling semiconductor material cools the outer surface of the catheter. This cooling occurs over a period of time until the outer surface of the catheter reaches a temperature, the temperature of the outer surface of the catheter being selected such that the circulating blood in contact with the outer surface of the catheter cools to a systemic temperature. The systemic temperature is selected to reduce or prevent an effect of a cardiac episode. In some implementations, the cardiac episode is myocardial infarction, and the effect of the myocardial infarction is myocardial scarring. Therefore, pumps configured with a Peltier device can provide support to the heart to prevent the negative effects of induced systemic hypothermia while still inducing systemic hypothermia in order to treat or prevent a negative effect of a cardiac episode.

In certain implementations of the method, a first blood pump comprising a Peltier device is introduced to one side of the heart of the patient and a second blood pump comprising a Peltier device is introduced to the other side of the heart of the patient. In some implementations, the first blood pump comprising a Peltier device is introduced into the right side of the heart of the patient, and the second blood pump comprising a Peltier device is introduced into the left side of the heart of the patient. In other implementations, the first blood pump comprising a Peltier device is introduced into the left side of the heart of the patient, and the second blood pump comprising a Peltier device is introduced into the right side of the heart of the patient. Such implementations comprise simultaneously cooling and unloading both sides of the heart of the patient. Simultaneously unloading and cooling both sides of the heart allows for the practitioner to cool the blood in the heart more rapidly, preventing the effects of cardiac episodes while at the same time, preventing the negative effects of induced systemic hypothermia by unloading the heart.

BRIEF DESCRIPTION OF THE DRAWINGS

FIG. 4. shows an illustrative method for simultaneously treating myocardial infarction while unloading the heart;

FIG. 5 shows an illustrative method for simultaneously treating myocardial infarction while unloading the heart using a mechanical circulatory support system configured with a lumen;

FIG. 6 shows an illustrative method for simultaneously treating myocardial infarction while unloading the heart using a mechanical circulatory support system configured with a Peltier device.

DETAILED DESCRIPTION

To provide an overall understanding of the systems, method, and devices disclosed herein, certain illustrative embodiments will be described. Although the embodiments and features described herein are specifically described for use in connection with a pump for a heart, it will be understood that the teachings may be adapted and applied to other pumps and other types of medical devices.

The systems, methods, and devices described herein provide a mechanical circulatory support system for a heart that is configured to simultaneously unload the heart while also inducing hypothermia within a patient so as to cool the blood of the patient in order to reduce or prevent a detrimental effect of a cardiac episode. Specifically, the systems, methods, and devices described herein provide a pump having a systemic cooling element along a length of a catheter of the pump, the cooling element being configured to induce hypothermia within the heart of a patient in order to reduce or prevent scarring incurred by myocardial infarction.

Figure 1:
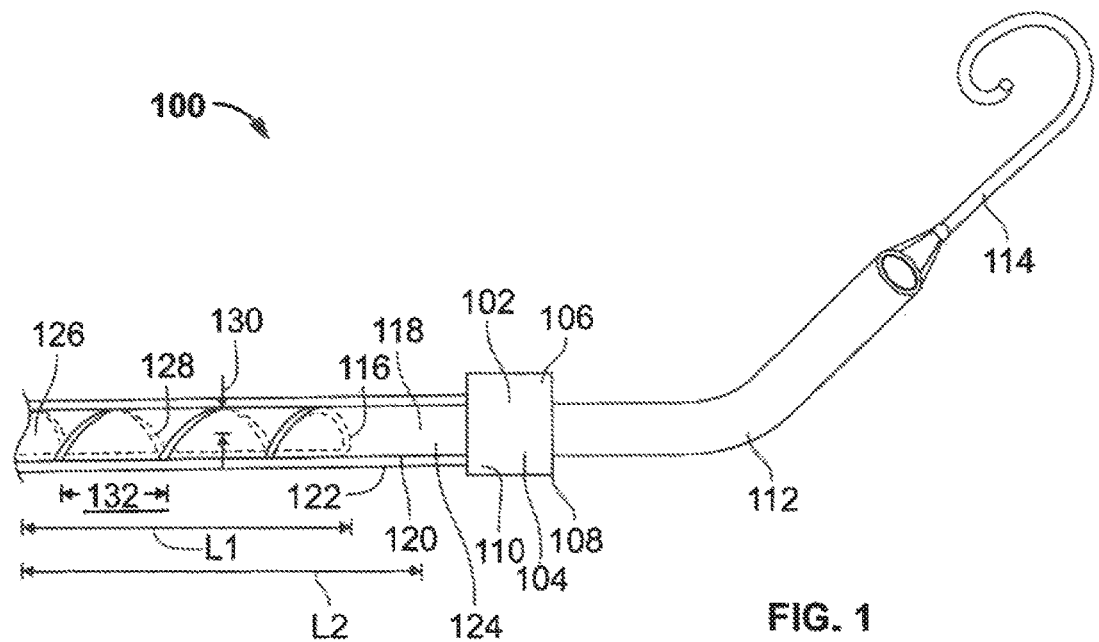
FIG. 1 shows an illustrative example of a mechanical circulatory support system for a heart having a cooling element.
Figure 7:
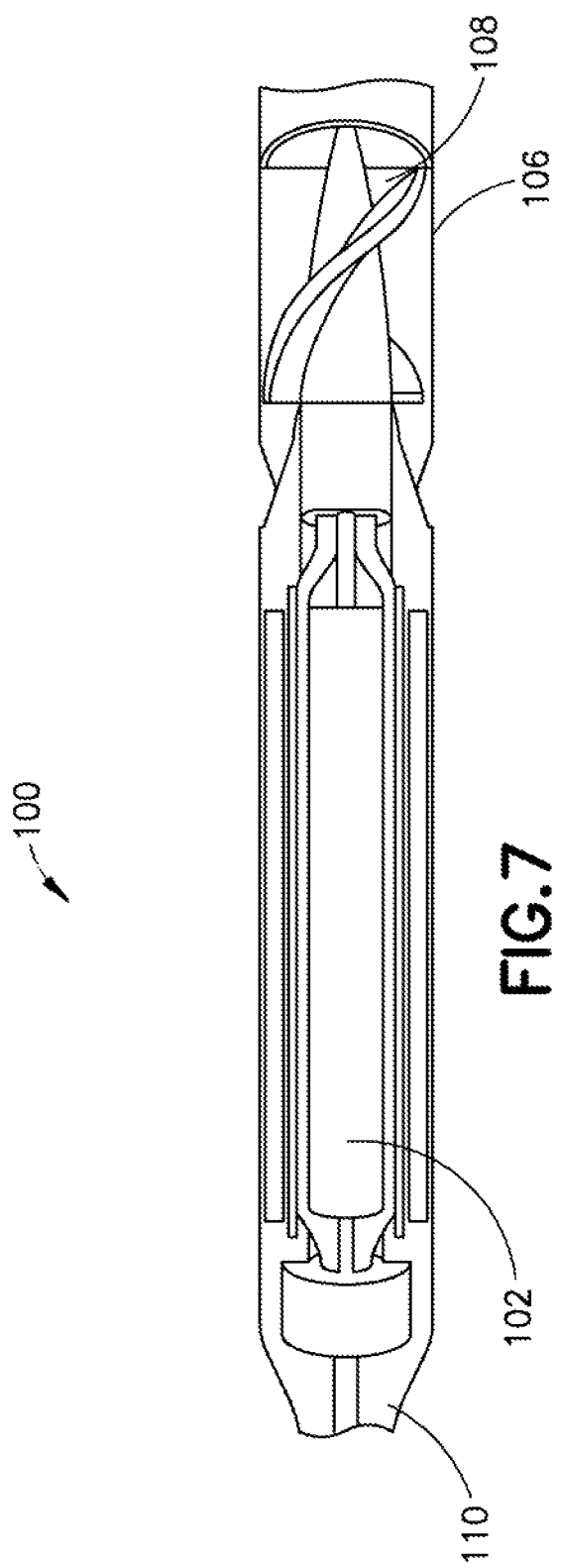
FIG. 7 is a detail view of a pump portion of the mechanical circulatory support system of FIG. 1.

FIG. 1 shows an illustrative example of a mechanical circulatory support system, or blood pump, for a heart 100 having a cooling element so that the pump can simultaneously unload the heart while inducing hypothermia within the patient. Illustrative FIG. 1 shows a cooling element extending along a single helix as it extends in one direction along the length of the catheter. As previously discussed, a single helix as defined herein refers to a single strand shaped as a helix. Heart pump 100 further comprises rotor 102, motor 104, pump housing 106 having distal end 108 and proximal end 110, cannula 112, distal extension 114, cooling element 116, and catheter 118 having inner surface 120, outer surface 122, distal end 124, and proximal end 126. Heart pump 100 with rotor 102, motor 104 and pump housing 106 are illustrated in more detail in FIG. 7. Cooling element 116 has diameter 128, and catheter 118 has radius 130. The helix formed by cooling element 116 has pitch 132. Catheter 118 extends in the proximal direction from the proximal end 110 of pump housing 106. Cooling element 116 is configured within catheter 118. As shown in FIG. 1, cooling element 116 extends along a length L1 of catheter 118 prior to turning back on itself. However, cooling element 116 may be configured to extend along illustrative length L2 of catheter 118, or along any other length of catheter 118 such that systemic cooling of the blood of a patient can be achieved when blood pump 100 is deployed within the heart or within other portions of the vasculature. Cooling element 116 is therefore generally configured to extend the length of catheter 118 twice. Cooling element 116 extends along a first length from proximal end 126 of catheter 118 to distal end 124 of catheter 118, and a second length from distal end 124 of catheter 118 to proximal end 126 of catheter 118. At least one advantage of the incorporation of cooling element 116 within catheter 118 is that the system can simultaneously induce hypothermia within the heart of a patient in order to prevent or reduce detrimental effects of cardiac episodes while also unloading the heart so as to prevent the detrimental effects that are commonly encountered upon inducing hypothermia into the heart of a patient. The cardiac episode that necessitates the use of such a pump may be myocardial infarction or a heart attack, and the effect of such an episode may be myocardial scarring. The decrease in temperature of the blood of a patient subject to induced hypothermia may generally slow down one or more biological processes responsible for the creation of myocardial scarring, thereby helping to prevent long-term damage to the heart after a patient suffers a cardiac episode.

Cooling element 116 may be configured within the catheter in a variety of different geometries. As previously discussed, cooling element 116 may extend along any suitable length of catheter 118 prior to turning back on itself. Two such illustrative lengths, L1 and L2, are shown in FIG. 1. The cooling element 116 may extend along any other suitable length of catheter 118. Additionally, cooling element 116 may be oriented in different geometries along each of the two lengths of catheter 118 along which cooling element 116 extends. For example, in illustrative FIG. 1, cooling element 116 extends from proximal end 126 of catheter 118 to distal end 124 of catheter 118 in a straight line. Once cooling element 116 extends along length L1, it may turn back and extend along a helix as it extends from distal end 124 of catheter 118 to proximal end 126 of catheter 118. In FIG. 1, the helix along which cooling element 116 extends from distal end 124 of catheter 118 to proximal end 126 of catheter 118 may be confined to inner surface 120 of catheter 118. In implementations in which cooling element 116 is a lumen, a chilled solution is injected into cooling element 116. As previously discussed, for a given geometry of a cooling element 116 comprising a lumen, the flow direction of the chilled solution within the lumen is reversible. In such implementations, the chilled fluid may be injected into either length of element 116 such that the chilled solution may either first extend down the straight-line portion of element 116 and then extend back towards proximal end 126 of catheter 118 along the helical portion of element 116 or the chilled fluid may first extend down the helical portion of cooling element 116 and then extend back towards proximal end 126 of catheter 118 along the straight-line portion of element 116.

The pitch 132 of the helix along which cooling element 116 extends from distal end 124 of catheter 118 to proximal end 126 of catheter 118 may vary between embodiments. For example, the pitch 132 of the helix along which cooling element 116 extends may be between about 1 millimeter and about 21 millimeters. In some implementations, the pitch 132 of the helix along which cooling element 116 extends may be between about 3 millimeters and about 19 millimeters. In other implementations, the pitch 132 of the helix along which cooling element 116 extends may be between about 5 and about 17 millimeters. In certain implementations, the pitch 132 of the helix along which cooling element 116 extends may be between about 7 millimeters and about 15 millimeters. In further implementations, the pitch 132 of the helix along which cooling element 116 extends may be between about 9 millimeters and about 13 millimeters. In other implementations, the pitch 132 of the helix along which cooling element 116 extends may be about 11 millimeters. At least one advantage of the variable pitch 132 of the helix formed by cooling element 116 is that the specific geometry of the cooling element can be selected to yield a desired interior surface area covered by cooling element 116.

Similarly, diameter 128 may be selected to achieve a desired covered interior surface area. For example, diameter 128 may be between about 0.5 millimeters and about 7.5 millimeters. In other implementations, diameter 128 may be between about 1 millimeter and about 7 millimeters. In further implementations, diameter 128 may be between about 1.5 millimeters and about 6.5 millimeters. In certain implementations, diameter 128 may be between about 2 millimeters and about 6 millimeters. In other implementations, diameter 128 may be between about 2.5 millimeters and about 5.5 millimeters. In other implementations, diameter 128 may be between about 3 millimeters and about 5 millimeters. In further implementations, diameter 128 may be about 4 millimeters.

The distance between the straight-line portion of cooling element 116 and inner surface 120 of catheter 118 can also be adjusted to yield a specific temperature profile along the length of the device. For example, the straight-line portion of cooling element may extend directly down the center of catheter 118. In other implementations, the straight-line portion of cooling element may extend down the length of the catheter 118 halfway between the center of catheter 118 and inner surface 120 of catheter 118. A smaller distance between straight-line portion of cooling element 116 and inner surface 120 of catheter 118 corresponds to a lower temperature of outer surface 122 of catheter 118. Conversely, a larger distance between straight-line portion of cooling element 116 and inner surface 120 of catheter 118 corresponds to a higher temperature of outer surface 122 of catheter 118.

In some implementations, cooling element 116 extends along a first helix as it extends from proximal end 126 of catheter 118 to distal end 124 of catheter 118. Once the first helix extends along a desired length along catheter 118, it may then turn back on itself and form a second helix as it extends from distal end 124 of catheter 118 to proximal end 126 of catheter 118. These two helices may be circumferentially offset from one another by an angle ranging between 0 degrees and 180 degrees.

Implementations in which the angle between the two helices is 180 degrees define a cooling element configured as a double helix. In such implementations, once the first helix extends along the first length along catheter from proximal end 126 of catheter 118 to distal end 124 of catheter 118, it may extend along a half-circumference of catheter 118 at a given longitudinal point along the length of catheter 118. After extending along this half-circumference, the second helix along which cooling element 116 extends may extend along the second length of catheter 118 from distal end 124 of catheter 118 to proximal end 126 of catheter 118. The double helix formed by cooling element 116 may have a variable pitch. For example, the pitch of the double helix along which cooling element 116 extends may be between about 1 millimeter and about 21 millimeters. In some implementations, the pitch of the double helix along which cooling element 116 extends may be between about 3 millimeters and about 19 millimeters. In other implementations, the pitch of the double helix along which cooling element 116 extends may be between about 5 and about 17 millimeters. In certain implementations, the pitch of the double helix along which cooling element 116 extends may be between about 7 millimeters and about 15 millimeters. In further implementations, the pitch of the double helix along which cooling element 116 extends may be between about 9 millimeters and about 13 millimeters. In other implementations, the pitch of the double helix along which cooling element extends may be about 11 millimeters. As previously discussed, implementations in which the angle between the two helices is 0 degrees define a cooling element configured as a double-wide single helix. A double-wide single helix as defined above comprises two single helices of the same pitch and of the same radius that are in contact at every point along their lengths.

In some implementations, catheter radius 130 may correspond to the radii of the helices formed by cooling element 116. In such implementations, cooling element 116 is confined to inner surface 120 of catheter 118. In other implementations, catheter radius 130 may be larger than one or both of the radii of the helices formed by cooling element 116. For example, the first helix formed by cooling element 116 may be confined to inner surface 120 of catheter 118, while the second helix may have a radius that is between about 1/6 and about 5/6 of catheter radius 130. In other implementations, the radius of the second helix is between about 1/3 and about 2/3 of catheter radius 130. In further implementations, the second helix formed by element 116 may have a radius of about 1/2 catheter radius 130. In implementations where the angle of offset between the first helix and the second helix is not 180 degrees, the two helices may form a single double-wide helix. Such a configuration is discussed further below in relation to FIG. 3.

Figure 2:
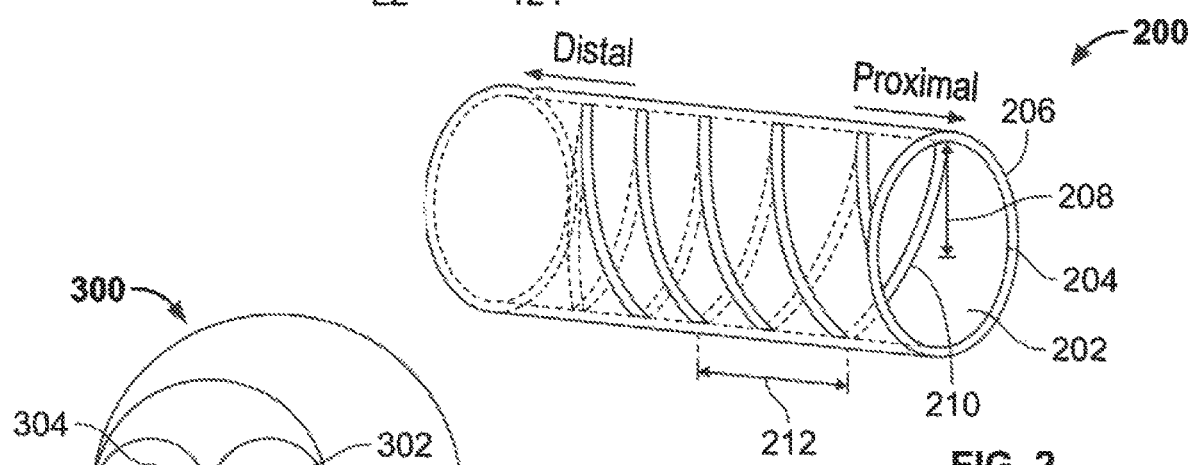
FIG. 2 shows an illustrative perspective view of a portion of a mechanical circulatory support system for a heart having a cooling element.

FIG. 2 shows an illustrative perspective view of a portion of a mechanical circulatory support system, or blood pump, for a heart 200 having a cooling element 210 configured in a double helix. Illustrative blood pump system 200 comprises catheter 202 having inner surface 204, outer surface 206, and radius 208 and cooling element 210. In FIG. 2, cooling element 210 is arranged in a double helix, comprising two single helices having pitch 212. The double helix of cooling element 210 as shown in illustrative FIG. 2 has a radius equivalent to catheter radius 208. As such, cooling element 210 as shown in FIG. 2 is confined to the inner surface 204 of catheter 202. In some implementations, catheter radius 208 may be larger than one or both of the radii of the helices formed by cooling element 210. For example, the first helix formed by cooling element 210 may have a radius equivalent to catheter radius 208 such that it is confined to inner surface 204 of catheter 202, while the second helix may have a radius that is between about 1/6 and 5/6 of catheter radius 208. In other implementations, the radius of the second helix is between about 1/3 and 2/3 of catheter radius 208. In further implementations, the second helix formed by element 210 may have a radius of about 1/2 catheter radius 208. In other implementations, both the first helix and the second helix have radii that are less than catheter radius 208. For example, in some implementations, the first and second helices have radii between about 1/6 and about 5/6 of catheter radius 208. In other implementations, the first and second helices have radii between about 1/3 and about 2/3 of catheter radius 208. In certain implementations, the first and second helices have radii between about 1/3 and about 2/3 of catheter radius 208.

As discussed previously in relation to FIG. 1, the first and second helices formed by element 210 may be circumferentially offset from one another by an angle ranging between 0 degrees and 180 degrees. As such, the first and second helices formed by element 210 may be configured as a double helix or as a double-wide single helix. In the illustrative embodiment of FIG. 2, the first and second helices are offset by an angle of 180 degrees such that they form a double helix, as defined above. As discussed below in relation to FIG. 3, the two helices may be offset by an angle of zero degrees such that they formed a double-wide single helix along a length of catheter 202.

In some implementations, cooling element 210 forms only one helix along a length of catheter 202. For example, cooling element 210 may extend in one direction down the center of catheter 202 and may extend in the other direction in the form of a helix along inner surface 204 of catheter 202. The specific geometry of cooling element 210 within catheter 202 can be adjusted in order to yield a specific temperature profile along the length of catheter 202.

Figure 3A:
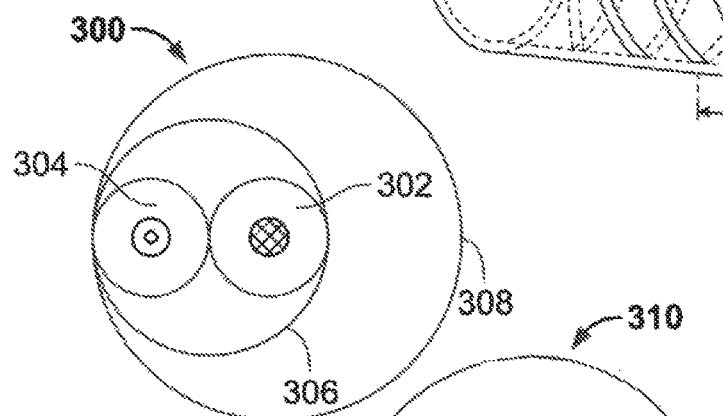
FIGS. 3A-3C show an illustrative example of a cross-section of a double-wide single helix.
Figure 3B:
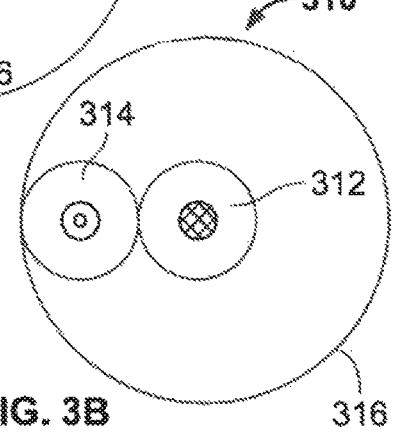
Figure 3C:
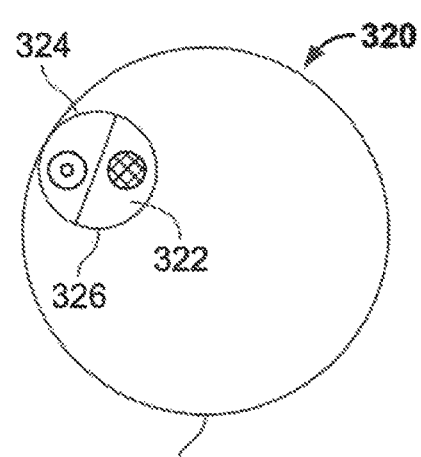

FIGS. 3A, 3B, and 3C show three illustrative examples of cross-sections of a catheter containing a cooling element for use in a mechanical circulatory support system, or blood pump, for a heart. FIGS. 3A, 3B, and 3C depict cross-sections of a catheter containing a lumen configured as a cooling element, but, as previously discussed, the cooling element may also be a Peltier device. FIG. 3A shows an illustrative cross-section of a cooling element for use in a blood pump system for a heart 300 having first lumen 302, second lumen 304, lumen channel 306, and catheter 308. In FIG. 3A, first lumen 302 and second lumen 304 are contained within lumen channel 306. Lumen channel 306 is contained within catheter 308. In FIG. 3A, first lumen 302 accommodates flow in a first direction, the first direction being from the proximal end of the catheter to the distal end of the catheter, while second lumen 304 accommodates flow in a second direction, the second direction being from the distal end of the catheter to the proximal end of the catheter. FIG. 3B shows another illustrative cross-section of a cooling element for use in a blood pump for a heart 310 having first lumen 312, second lumen 314, and catheter 316. In FIG. 3B, first lumen 312 accommodates flow in a first direction, the first direction being from the proximal end of the catheter to the distal end of the catheter, while second lumen 314 accommodates flow in a second direction, the second direction being from the distal end of the catheter to the proximal end of the catheter. FIG. 3C shows a third illustrative cross-section of a cooling element for use in a blood pump for a heart 320 having first lumen portion 322, second lumen portion 324, lumen channel 326, and catheter 328. In FIG. 3C, first lumen portion 322 and second lumen portion 324 are contained within lumen channel 326. Specifically, lumen channel 326 is divided into two portions, first lumen portion 322 comprising a first lumen and second lumen portion 324 comprising a second lumen. First lumen portion 322 and second lumen portion 324 may be oriented within lumen channel 326 in a variety of configurations. For example, as shown in FIG. 3C, first lumen portion 322 and second lumen portion 324 may both comprise one half of lumen channel 326. In other implementations, first lumen portion 322 may comprise a larger portion of lumen channel 326 than does second lumen portion 324. In other implementations, first lumen portion 322 may comprise a smaller portion of lumen channel 326 than does second lumen portion 324. Lumen channel 326 is contained within catheter 328. In FIG. 3C, first lumen 322 accommodates flow in a first direction, the first direction being from the proximal end of the catheter to the distal end of catheter 328, while second lumen 324 accommodates flow in a second direction, the second direction being from the distal end of the catheter to the proximal end of catheter 328. In configurations having a Peltier device as the cooling element, the semiconductors of the Peltier device may similarly be oriented in a variety of configurations and relative shapes and sizes. For example, the first semiconductor material of the Peltier device may be configured against the inner surface of the catheter in the shape of the inner surface of the catheter, while the second semiconductor material may be cylindrical and extending along the center of the catheter. The first semiconductor material may further be embedded within a wall of the catheter. In some implementations, the first semiconductor material may have a surface area that is greater than a surface area of the second semiconductor material. In other implementations, the first semiconductor material may have the same surface area as the second semiconductor material. In certain implementations, the first semiconductor material may have a smaller surface area than the second semiconductor material.

FIG. 4 shows an illustrative method 400 for simultaneously treating myocardial infarction while unloading the heart. Method 400 first comprises step 402 of introducing a mechanical circulatory support system into the left side of the heart of a patient. The mechanical circulatory support system may be a blood pump. The pump of method 400 comprises a cooling element configured within a catheter. Such a cooling element is configured to receive either a chilled solution or an electric current, and the cooling element is configured to be in contact with an inner surface of the catheter such that blood that is in contact with an outer surface of the catheter is cooled. Subsequently, a practitioner executing method 400 performs step 404, comprising actuating the pump using an on-board motor. After the pump has been actuated, the practitioner then performs step 406 of activating the cooling element to cool the blood that is in contact with the outer surface of the catheter. In step 406, the blood is cooled for a period of time such that the blood reaches a systemic temperature. For example, the blood may be systemically cooled for a time period of between about 5 minutes and about 20 minutes. In other implementations, the time period is between about 7.5 minutes and about 17.5 minutes. In further implementations, the time period is between about 10 and about 15 minutes. In some implementations, the time period over which the blood is cooled to the systemic temperature is about 12.5 minutes. The systemic temperature is selected to reduce or prevent an effect of a cardiac episode. In some implementations, the cardiac episode being treated or prevented is myocardial infarction, and in some implementations, the effect of the myocardial infarction being treated or prevented is myocardial scarring. The cooling of the blood circulating through the heart slows down the biological processes that cause myocardial scarring, which reduces and prevents the heart of a patient from scarring after myocardial infarction. The inclusion cooling element induces hypothermia within the patient, while the support offered by the blood pump helps to unload the heart, preventing or reducing negative side effects of induced hypothermia, including induced arrhythmias.

FIG. 5 shows an illustrative method 500 for simultaneously treating myocardial infarction while unloading the heart using a mechanical circulatory support system configured with a lumen. The mechanical circulatory support system may be a blood pump. In other implementations, the mechanical circulatory support system may be an intra-aortic balloon pump, a left-heart support system, or a right-heart support system. As discussed above, the lumen of the mechanical circulatory support system of the method may be configured in a variety of geometries. For example, the lumen may extend along a helix in one direction along the length of the catheter, as shown in FIG. 1. In other implementations, the lumen may form a double helix, as shown in FIG. 2. Method 500 first comprises step 502 of introducing a blood pump into the left side of the heart of a patient. The pump of method 500 comprises a lumen configured to receive a chilled fluid. As previously discussed, the chilled solution may comprise a crystalloid fluid. The crystalloid fluid may be Normal saline (a solution comprising 9 grams of sodium chloride per liter of solution), Lactated Ringer's solution, ⅓ NS ⅔D5, or glucose. Generally, the solution with the highest heat capacity is selected, as such a solution will be able to cool the blood most rapidly without experiencing an increase in temperature, allowing the solution to remain in contact with the inner surface of catheter along both lengths of the catheter. For any geometry, at least a portion of the lumen is in contact with an inner surface of the catheter and, the lumen is configured to cool blood in contact with an outer surface of the catheter. A practitioner performing method 500 then actuates the pump using an on-board motor in step 504. While actuating the pump, the practitioner injects the chilled solution into the lumen to cool the blood that is in contact with the outer surface of the catheter in step 506. In step 506, the blood is cooled for a period of time such that the blood reaches a systemic temperature. The systemic temperature is selected to reduce or prevent an effect of a cardiac episode. As previously discussed, the temperature of the chilled solution is selected such that the blood reaches a systemic temperature and becomes cold enough to slow the biological processes responsible for causing detrimental effects to a patient after the patient suffers a cardiac episode. The cardiac episode may be myocardial infarction, and the effect of the myocardial infarction may be scarring. The simultaneous cooling and unloading of the heart allow hypothermia to be induced by the cooling element while the blood pump prevents the negative effects of induced hypothermia.

FIG. 6 shows an illustrative method 600 for simultaneously treating myocardial infarction while unloading the heart using a mechanical circulatory support system configured with a Peltier device. The mechanical circulatory support system may be a blood pump. Method 600 first comprises step 602 of introducing a blood pump into the left side of the heart of a patient. The pump of method 600 comprises a Peltier device. The Peltier device drives the transfer of heat between two semiconductor materials having different properties. For example, the electron densities of the two semiconductor materials may be different. The Peltier device can be configured in a variety of geometries. Particularly, the Peltier device comprises two semiconductor materials forming a junction which may be arranged in a variety of different configurations in order to direct heat flow in the desired direction and to the desired portions of the device. For example, the semiconductor materials may be oriented such that heat flow is directed in a radial direction, or the semiconductor materials may be oriented such that heat flow is directed longitudinally along the length of the catheter. The semiconductor materials may further be arranged in any configuration that allows for a current to be delivered to a junction formed by the semiconductor materials. The junction of the two semiconductor materials having different electron densities may be located at any suitable point along the length of the catheter in order to establish a certain heat distribution along the length of the catheter. In some implementations, the junction of the two semiconductor materials having different electron densities is located at the distal end of the catheter. In other implementations, the junction of the two semiconductor materials having different electron densities is located at the proximal end of the catheter. One of the semiconductor materials is in contact with an inner surface of the catheter, such that it is configured to cool blood in contact with an outer surface of the catheter. After introducing the pump, a practitioner then actuates the pump using an on-board motor in step 604. While actuating the pump, at step 606, an electric current is run through the first wire to the junction of the semiconductor materials of the Peltier device cool the blood that is in contact with the outer surface of the catheter. The current delivered to the junction of the semiconductor materials of the Peltier device may range between about 0.01 Amperes and about 3 Amperes. In some implementations, a current between about 0.1 Amperes and about 2 Amperes is delivered to the junction of the semiconductor materials of the Peltier device. In further implementations, a current between about 0.5 Amperes and 1.5 Amperes is delivered to the junction of the semiconductor materials of the Peltier device. In certain implementations, a current of about 1 Ampere is delivered to the junction of the semiconductor materials of the Peltier device. The particular current run through the wire of the Peltier device can be adjusted to create a certain potential difference at the junction of the semiconductor materials, allowing for a certain heat distribution and rate of cooling of the blood to be implemented along the catheter. The blood is cooled for a period of time such that the blood reaches a systemic temperature. For example, the blood may be systemically cooled for a time period of between about 5 minutes and about 20 minutes. In other implementations, the time period is between about 7.5 minutes and about 17.5 minutes. In further implementations, the time period is between about 10 and about 15 minutes. In some implementations, the time period over which the blood is cooled to the systemic temperature is about 12.5 minutes. The systemic temperature selected to reduce or prevent an effect of a cardiac episode. The cardiac episode may be myocardial infarction, and the effect of the myocardial infarction to be treated may be myocardial scarring.

The foregoing is merely illustrative of the principles of the disclosure, and the apparatuses can be practiced by other than the described aspects, which are presented for purposes of illustration and not of limitation. It is to be understood that the apparatuses disclosed herein, while shown for use in pumps, may be applied to other apparatuses. Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:
1. A mechanical circulatory support system for a heart, the mechanical circulatory support system comprising:
    a pump having a distal end and a proximal end, the pump comprising a rotor, the rotor having at least one blade;
    a pump housing, the pump housing surrounding the at least one blade of the rotor;
    a catheter having a distal end, a proximal end, an inner surface, and an outer surface, the catheter extending proximally relative to the pump housing, the outer surface of the catheter configured to contact blood when disposed within patient vasculature; and a cooling element configured to cool the blood that comes in contact with the outer surface of the catheter, wherein the cooling element is formed as a lumen configured to receive a chilled solution.

2. The mechanical circulatory support system of claim 1, wherein the cooling element is configured to cool the outer surface of the catheter.

3. The mechanical circulatory support system of claim 1, wherein the cooling element extends within the catheter.

4. The mechanical circulatory support system of claim 1, wherein the cooling element is configured to cool the inner surface of the catheter.

5. The mechanical circulatory support system of claim 4, wherein cooling of the inner surface is configured to conduct thermal energy away from the outer surface of the catheter to cool the outer surface.

6. The mechanical circulatory support system of claim 5, wherein the cooling element is configured to cool the outer surface of the catheter.

7. The mechanical circulatory support system of claim 1, wherein the lumen is configured to extend along a length of the catheter twice.

8. The mechanical circulatory support system of claim 1, wherein the lumen has a first proximal opening and a second proximal opening, the first proximal opening configured as an inlet for the chilled solution and the second proximal opening serving as an outlet for the chilled solution.

9. The mechanical circulatory support system of claim 8, wherein a first flow portion along which the lumen extends is from the proximal end to the distal end, and a second flow portion along which the lumen extends is from the distal end to the proximal end.

10. The mechanical circulatory support system of claim 9, wherein the first flow portion extends from the first proximal opening to the distal end of the catheter.

11. The mechanical circulatory support system of claim 9, wherein the first flow portion accommodates a flow of the chilled solution from the proximal end of the catheter to the distal end of the catheter.

12. The mechanical circulatory support system of claim 9, wherein the second flow portion extends from the distal end of the catheter to the second proximal opening.

13. The mechanical circulatory support system of claim 9, wherein the second flow portion accommodates a flow of the chilled solution from the distal end of the catheter to the proximal end of the catheter.

14. The mechanical circulatory support system of claim 8, wherein the chilled solution comprises a crystalloid fluid.

15. The mechanical circulatory support system of claim 14, wherein the crystalloid fluid is a normal saline solution.

16. The mechanical circulatory support system of claim 1, wherein the cooling element cools the blood that is in contact with the outer surface of the catheter to a systemic temperature.

17. The mechanical circulatory support system of claim 16, wherein the systemic temperature is about 32 to about 33 degrees Celsius.

18. The mechanical circulatory support system of claim 1, wherein the lumen is configured to deliver the chilled solution along a length of the catheter.

* * * * *